United States Patent [19]

Itoh et al.

[11] 4,201,769
[45] May 6, 1980

[54] ANTIBIOTIC SUBSTANCES NO. 17927A$_1$ AND NO. 17927A$_2$ AND PROCESS FOR PRODUCING THE SAME

[75] Inventors: Yasuhiro Itoh; Masaki Nakahara; Yo Takiguchi; Mamoru Arai; Tatsuo Haneishi; Masatoshi Inukai; Mutsuo Nakajima, all of Hiromachi, Japan

[73] Assignee: Sankyo Company Limited, Tokyo, Japan

[21] Appl. No.: 882,187

[22] Filed: Feb. 28, 1978

[30] Foreign Application Priority Data

Mar. 4, 1977 [JP] Japan .................................. 52-23663

[51] Int. Cl.$^2$ ........................ A61K 35/74; C12P 1/06
[52] U.S. Cl. .................................... 424/117; 435/169
[58] Field of Search ............. 195/80 R; 424/118, 117; 435/169

[56] References Cited

U.S. PATENT DOCUMENTS

| | | | |
|---|---|---|---|
| 3,377,243 | 4/1968 | Voe et al. | 424/118 |
| 3,629,404 | 12/1971 | Florent et al. | 424/118 |
| 3,919,415 | 11/1975 | Butterworth et al. | 195/80 R |
| 3,928,569 | 12/1975 | Umezawa et al. | 195/80 R |

*Primary Examiner*—Alvin E. Tanenholtz
*Attorney, Agent, or Firm*—Frishauf, Holtz, Goodman & Woodward

[57] ABSTRACT

New antibiotic substances named substance No. 17927A$_2$ and substance No. 17927A$_1$ produced by cultivation of substances No. 17927A$_2$ and No. 17927A$_1$-producing microorganisms belonging to the genus Streptomyces as well as pharmaceutically-acceptable salts thereof. They have broad antibacterial activities and also $\beta$-lactamase inhibitory action so that they show synergistic actions with known penicillins and cephalosporins.

7 Claims, 6 Drawing Figures

ANTIBIOTIC SUBSTANCES NO. 17927A₁ AND NO. 17927A₂ AND PROCESS FOR PRODUCING THE SAME

This invention relates to new antibiotic substances named substance No. $17927A_2$ and No. $17927A_1$ and also to a fermentative process for producing the same.

We have found that actinomycetes such as the strain No. 17927 isolated from a soil sample collected at Hikone, Shiga-prefecture, the strain No. 18032 isolated from a soil sample collected at Nichinan-city, Miyazaki-prefecture, the strain No. 18333 isolated from a soil sample collected at Toyono, Osaka-city can produce identical new antibiotic substances, substance No. $17927A_2$ and substance No. $17927A_1$. Also, as a result of investigation on properties of these actinomycetes, all three strains have been identified as *Streptomyces fulvoviridis* as fully mentioned hereinbelow. Then, further investigations have been made on cultured broth of known *Streptomyces fulvoviridis*, for example, the *Streptomyces fulvoviridis* as disclosed in Japanese Provisional Publication Nos. 135294/1975, 140692/1975 and 118701/1976 (These specifications describe production of antibiotic substances named MM 4550, MM 13902 and MM 17880, respectively, but these antibiotic substances are definitely distinct from the substance No. $17927A_1$ and the substance No. $17927A_2$.) and related microorganisms. As a result, it has been recognized that such strains as *Streptomyces fulvoviridis* ATCC 15863, *Streptomyces olivaceus* ATCC 31126, *Streptomyces argenteolus* ATCC 11009 and the like can produce the substances No. $17927A_2$ and No. $17927A_1$ simultaneously with MM 4550, MM 13902 and MM 17880.

The present substances No. $17927A_2$ and No. $17927A_1$ show an extremely potent antibacterial activity against gram-positive and gram-negative bacteria including clinical isolates resistant to known antibiotic substances and also a synergistic effect in combination with known penicillin-type and cephalosporin-type antibiotic substances, since the substances No. $17927A_2$ and No. $17927A_1$ can act as an inhibitory substance of β-lactamase against the β-lactamase-producing strains among these resistant microorganisms. Therefore, the substances No. $17927A_2$ and No. $17927A_1$ is applicable for the treatment of human, animal and plant diseases caused by a wide variety of such gram-positive and gram-negative bacteria.

Morphological properties of the isolated actinomycetes three strains No. 17927, No. 18032 and No. 18333 as mentioned above, which can produce the new antibiotic substances, substance No. $17927A_2$ and substance No. $17927A_1$ having an inhibitory action of β-lactamase, are summarized as below.

(1) Morphological characteristics

Sporophores are Rectus-Flexibilis and generally long. A spore chain has 10 to 50 or more spores. Spores are mostly elliptical in shape and have a smooth surface and about $0.8-1.1 \times 1.0-1.3\mu$ in size. Sporophores are monopodial-branching and not of a loop-, hook- or spiral-shape. No special organs such as flagellated spores, sporangia are formed. Sporophores are formed on aerial mycelia and substrate mycelia.

(2) Properties on culture media

Properties on various media when cultivated at 28° C. for 2 weeks are summarized in Table 1.

Table 1

| Medium | | No. 17927 | No. 18032 | No. 18333 | ISP 5210 |
|---|---|---|---|---|---|
| Sucrose-nitrate agar | G* | abundant | abundant | abundant | good |
| | AM** | gray | brownish white | brownish white | brownish white |
| | R*** | brownish gray to yellowish brown | brownish black | grayish yellowish brown | brownish gray |
| Glucose-asparagine agar | G | good | good | good | good |
| | AM | olive-gray | olive-gray | olive-gray | olive-gray |
| | R | yellowish brown | grayish olive | pale olive | grayish olive |
| Glycerol-asparagine agar (ISP 5) | G | good | good | good | abundant |
| | AM | gray | grayish brown | brownish gray | brownish gray |
| | R | yellowish brown | yellowish brown to brownish gray | yellowish brown | yellowish brown |
| Starch-inorganic salt agar (ISP 4) | G | abundant | abundant | good | abundant |
| | AM | brownish gray | brownish gray | brownish gray | brownish gray |
| | R | yellowish brown to yellowish brown | olive gray | yellowish brown | brownish gray |
| Tyrosine agar (ISP 7) | G | abundant | abundant | abundant | abundant |
| | AM | brownish gray | brownish gray | brownish gray | olive gray |
| | R | yellowish brown to brownish gray | grayish olive | pale olive | brownish gray |
| Nutrient agar (Difco) | G | good | good | scant | good |
| | AM | brownish white | brownish gray | brownish white | brownish white |
| | R | yellowish brown | brownish gray | yellowish brown | brownish gray |
| Yeast extract-malt extract agar (ISP 2) | G | abundant | abundant | abundant | abundant |
| | AM | gray | brownish white | brownish gray | brownish gray |
| | R | yellowish brown to brownish gray | brownish black | brown | dark brown |
| Oatmeal agar (ISP 3) | G | abundant | abundant | abundant | abundant |
| | AM | gray | brownish gray | gray | gray |
| | R | dark yellow | grayish olive | yellowish brown | yellowish brown to grayish olive |

*G: Growth. AM: Aerial mycelium. *R: Reverse

(3) Physiological properties

Physiological properties are summarized in Table 2.

Table 2

| | Physiological properties | | | |
|---|---|---|---|---|
| | No. 17927 | No. 18032 | No. 18333 | ISP 5210 |
| Tyrosinase reaction | — | — | — | — |
| Nitrate | — | — | — | — |

Table 2-continued

| | | Physiological properties | | | |
|---|---|---|---|---|---|
| | | No. 17927 | No. 18032 | No. 18333 | ISP 5210 |
| reduction | | | | | |
| Liquefaction of gelatin | | − | − | − | + |
| Melanin formation* | | − | − | − | − |
| Hydrolysis of starch | | ++ | + | ++ | ++ |
| Milk Coagulation | 26° C. | − | − | − | ± |
| | 37° C. | + | ++ | ++ | ++ |
| Milk Peptonization | 26° C. | +(pH6.2) | +(pH6.4) | − | ++(pH7.0) |
| | 37° C. | ++(pH6.4) | ++(pH6.2) | +(pH6.2) | ++(pH6.2) |

++: Strong positive. +: Positive. ±: Doubtful
−: Negative
*Productivity on Triptone . yeast extract . broth (ISP 1) and Peptone . yeast extract . iron agar (ISP 6) media (4) Carbon source utilization Carbon source utilization when cultivated on Pridham-Gottlieb agar medium at 28° C. for 2 weeks are summarized in Table 3.

Table 3

| | Carbon source utilization | | | |
|---|---|---|---|---|
| | No. 17927 | No. 18032 | No. 18333 | ISP 5210 |
| D-glucose | + | + | + | + |
| L-arabinose | + | ± | + | ± |
| D-xylose | + | + | ± | + |
| D-fructose | ++ | ± | + | ++ |
| L-rhamnose | ++ | + | + | + |
| i-inositol | − | − | − | − |
| D-mannitol | + | + | + | ± |
| sucrose | − | − | − | − |
| raffinose | − | − | − | − |
| D-galactose | ++ | + | + | ± |
| glycerol | + | − | ± | ++ |
| cellulose | − | − | + | − |

++: Utilization positive. +: Utilization observed.
±: Utilization doubtful or very minor.
−: Utilization negative In summary of the aforesaid properties, the three strains No. 17927, No. 18032 and No. 18333 have been regarded as being of the same species, though some differences were observed in carbon source utilization and others, and as belonging to the genus Streptomyces. Spore-forming mycelia are Rectus-Flexibilis, spores are elliptical and have a smooth surface. Growth on various media is good and gray or brownish gray aerial mycelia are formed on yellowish brown to brownish gray substrate mycelia. In regard to physiological properties, hydrolysis of starch, milk coagulation and milk peptonization are positive and melanin-like pigments are not generally produced. In carbon source utilization, glucose, rhamnose, mannitol, galactose and the like are positive and inositol, sucrose, raffinose and the like are negative.

Investigations about known strains having the aforesaid properties showed as the most related strain *Streptomyces fulvoviridis* [Buchanan, R.E. et al: Bergey's Manual of Determinative Bacteriology, the 8th Ed., p.758–759 (1974); Shirling, E.B. et al: International Journal of Systematic Bacteriology, Vol. 18, No. 4, p.321–322 (1968)].

Then, in comparing the strains No. 17927, No. 18032 and No. 18333 with *Streptomyces fulvoviridis* ISP 5210 strain by simultaneous cultivation, the difference between the above 3 strains, as shown in Tables 1–3, was observed in that liquefaction of gelatin is positive, that carbon source utilization is somewhat different and so on, but they showed the very identical properties in other points.

The strains No. 17927, No. 18032 and No. 18333 have, therefore, been identified as *Streptomyces fulvoviridis*.

All strains No. 17927, No. 18032 and No. 18333 have been deposited under the accession Nos. 3935, 3936 and 3937, respectively, with Technical Research Institute of Microbial Industry, Agency of Industrial Science & Technology, Ministry of International Trade and Industry, Japan.

The *Streptomyces fulvoviridis* is known as a microorganism capable of producing $\beta$-lactamase inhibitors, MC 696-SY2-A and MC 696-SY2-B (West German Patent Publication No. 2,340,005) and antibiotic substances, MM 4550, MM 13902 and MM 17880 (Japanese Patent Provisional Publication Nos. 135294/1975, 14692/1975 and 118701/1976), but these $\beta$-lactamase inhibitors and antibiotic substances are distinctly different from the substance No. 17927A$_1$ and substance No. 17927A$_2$ in various properties. However, when the microorganisms capable of producing MM 4550, MM 13902, MM 17880 were further studied for their produced antibiotic substances, it has been confirmed that *Streptomyces fulvoviridis* ATCC 15863, *Streptomyces olivaceus* ATCC 21379 and ATCC 31126 and *Streptomyces argenteolus* ATCC 11009 produced the substance No. 17927A$_1$ and substance No. 17927A$_2$ simultaneously with MM 4550, MM 13902, MM 17880.

In addition, the substances named C$_1$ and C$_2$ by the present inventors among the antibiotic substances produced by the No. 17927, No. 18032 and No. 18333 strains have been proved to be identical with MM 13902 and MM 17880, respectively. However, there is no disclosure about productivity of the substance No. 17927A$_2$ or substance No. 17927A$_1$ in the above-mentioned Japanese Patent Provisional Publications and thus the present antibiotic substances No. 17927A$_2$ and No. 17927A$_1$ have been identified as novel antibiotic substances producible by *Streptomyces fulvoviridis* and its related microorganisms.

Although has been explained the substance No. 17927A$_2$ or No. 17927A$_1$-producing strain in the foregoing, it is well-known that various properties of actinomycetes are not definite, but may be varied naturally and artificially. The strains which may be employed in this invention include all of the strains which belong to the genus Streptomyces and are capable of producing the substance No. 17927A$_2$ or No. 17927A$_1$.

Cultivation in the process of this invention may be carried out according to the method generally employed for actinomycetes. Shaken culture or submerged culture in a liquid medium is preferable. As medium components, there may be employed any of the well-known nutrient sources for actinomycetes. For instance, as a carbon source, glucose, glycerol, maltose, dextrin, starch, soybean oil, cotton seed oil etc.; as a nitrogen source, soybean meal, peanut meal, cotton seed meal, fish meal, corn steep liquor, peptone, meat extract, yeast, yeast extract, sodium nitrate, ammonium nitrate, ammonium sulfate, various amino acids etc.; as a sulfur source, sodium sulfate, sodium thiosulfate, cystein, methionine etc.; as an inorganic salt, sodium chloride, phosphate, calcium carbonate etc.; as a minor metal salt, ferrous sulfate, magnesium sulfate, zinc sulfate, manganese sulfate, cobalt sulfate etc. may be optionally added.

In carrying out liquid cultivation with aeration and agitation, an anti-foaming agent, e.g., silicone oil, vegetable oils, surfactants, etc. may be suitably employed.

The pH of the medium may be suitably within or around neutral range and cultivation temperature may be usually of 25°–30° C., in particular about 27° C. being preferred.

Change with time lapse in the activity of the antibiotic substance No. $17927A_2$ or No. $17927A_1$, which is produced in the cultured broth as the cultivation proceeds, can be determined by a well-known paper disc diffusion method using *Bacillus subtilis* PCI 219 as a test organism or an inhibitory action on β-lactamase produced by *Proteus morganii* 1510.

However, the present cultivation method provides the desired substances No. $17927A_2$ and No. $17927A_1$ simultaneously with other similar antibiotic substances, for example, the substances No. $17927C_1$ and No. $17927C_2$. Then, it is required for a quantitative determination of the substance No. $17927A_2$ or $A_1$ to employ a thin layer chromatography and a high voltage paper electrophoresis in combination therewith or, alternatively, to conduct such a determination of the substance No. $17927A_2$ after separation of some of the substance No. $17927A_2$ from other antibiotic substances, which is equally true with regard to the substance No. $17927A_1$.

Usually, the maximum productivity of the substance No. $17927A_2$ or No. $17927A_1$ is attained by cultivation for 50–150 hours.

The substance No. $17927A_2$ or No. $17927A_1$ is soluble in water and predominantly present in a liquid portion of a cultured broth. After completion of the cultivation, mycelia and other solid components are usually removed by a filtration procedure using diatomaceous earth as a filter aid or centrifugation and the substances No. $17927A_2$ and No. $17927A_1$ existing in the filtrate or the supernatant may be extracted and purified by utilizing their physico-chemical properties. For instance, the substances in a cultured broth may be recovered by the use of an adsorbent. As the adsorbent, there may be employed, for example, active carbon powder or special resinous adsorbents, e.g., Amberlite XAD-2, XAD-4 (available from Rohm & Haas Co., U.S.A.), Diaion.HP-10, HP-20, HP-30 (available from Mitsubishi Chemical Industries Ltd., Japan) and a liquid containing the substances No. $17927A_2$ and No. $17927A_1$ is passed through such an adsorbent and impurities are adsorbed thereon to remove them or the substances No. $17927A_2$ and $17927A_1$ are adsorbed on such an adsorbent and eluted with aqueous methanol, aqueous n-butanol or aqueous acetone. Also, at a pH around neutral the substances No. $17927A_2$ and No. $17927A_1$ are stable and act as an acidic substance, whereby the substances may be purified by adsorption and desorption on an anion exchanger. As the anion exchanger, there may be employed, for example, DEAE-cellulose (available from Brown Co., Inc., U.S.A.), DEAE-Sephadex, QAE-Sephadex (available from Pharmacia Co., Inc., U.S.A.), Duolite A-2, A-4 (available from Diamond Shamrock Chemical Co., Ltd., U.S.A.) Amberlite IRA-68 (available from Rohm & Haas Co., Ltd., U.S.A.), Dowex 1X4, Dowex 21K (available from Dow Chemical Co., Ltd., U.S.A.) and the like. Also, utilizing the above-mentioned properties of the acidic substance, there may be used a method wherein the substance No. $17927A_2$ or No. $17927A_1$ is extracted as the corresponding quaternary ammonium salt from an aqueous solution containing it by the use of a solution of a quaternary ammonium salt such as dimethyl benzyl cetyl ammonium chloride in a water-immiscible solvent such as dichloromethane.

The desired substances No. $17927A_2$ and No. $17927A_1$ can be easily separated or fractionated by a conventional chromatography on a column of the above-mentioned anion exchanger such as DEAE-cellulose, DEAE-Sephadex and the like. It may be generally observed that the substance No. $17927A_1$ is contained in the active fractions earlier eluted, while the substance No. $17927A_2$ is contained in the subsequently eluted fractions.

For further purification of the substance No. $17927A_2$ or No. $17927A_1$ there may be effectively used partition chromatography using cellulose, e.g., Avicel (available from Asahi Chemical Industry Co., Ltd., Japan) or silica gel as a carrier or gel filtration using an insoluble polymer, utilizing difference in a molecular weight, a molecular shape etc. As the carrier for gel filtration, there may be preferably employed Sephadex G-15 (available from Pharmacia Co., Ltd., Japan) Bio-gel P-2 (available from Bio Rad Laboratories, U.S.A.) and the like.

In purification of the substance No. $17927A_2$, it is necessary to conduct the procedures at a pH range of 6.0–8.0, preferably 7.0–7.5 and a lower temperature range of, e.g., 20° C. or lower, preferably 10° C. or lower.

A determination of the substance No. $17927A_2$ or No. $17927A_1$ during extraction and purification steps may be effected, as done in a cultured broth, by a paper disc diffusion method using *Bacillus subtilis* PCI 219 as a test organism or by an inhibitory action on β-lactamase produced by *Proteus morganii* 1510 and a test sample is diluted to a suitable concentration with a phosphate buffer of pH 7.0. As is in the case of a cultured broth, when there are present other antibiotic substances with β-lactamase inhibiting activity, determination is effected, if required, after isolating the substance No. $17927A_2$ or No. $17927A_1$. As a standard sample is used Cephaloridine and a concentration of the substance No. $17927A_2$ to produce the same inhibition zone as Cephaloridine 1 μg/ml is expressed as 1 unit/ml of the substance No. $17927A_2$ or No. $17927A_1$.

The substance No. $17927A_2$ or No. $17927A_1$ may be isolated and purified by any optional combination of the above-mentioned purification procedures or their repeated uses.

The substances No. $17927A_2$ and No. $17927A_1$ thus obtained have the following properties, which are shown with regard to the corresponding sodium salts, respectively.

Figure 1:
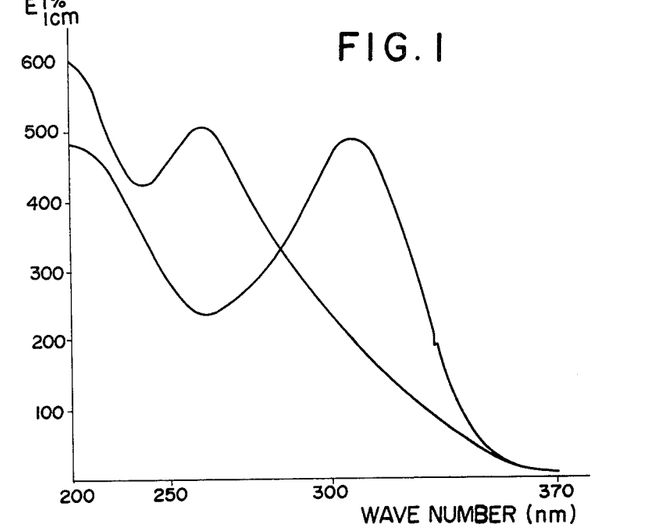
Figure 2:
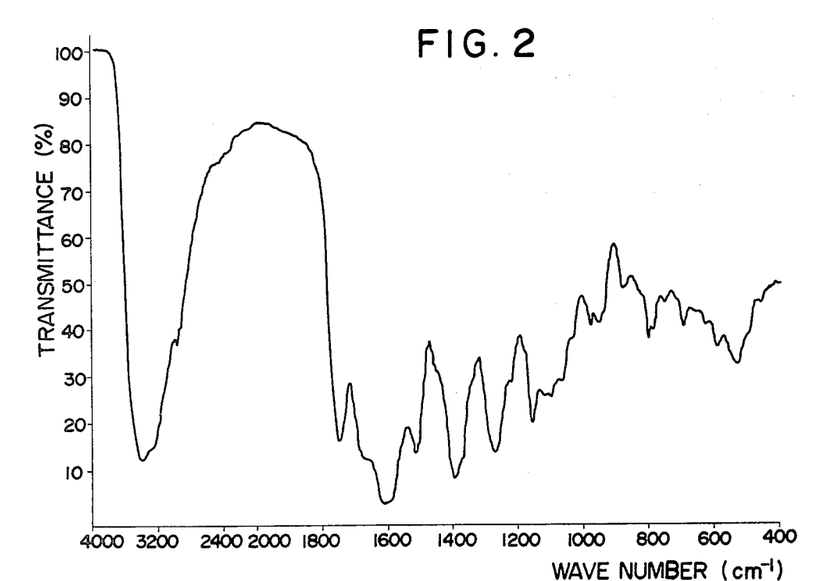
Figure 3:
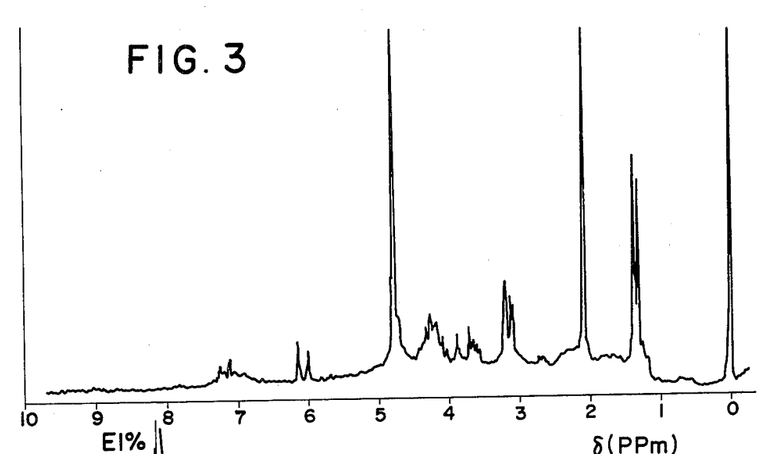

Substance No. 17927A$_2$ (1) Color and shape of the substance: Pale yellow powder when freeze-dried
(2) Analysis (Found): C, 46.52%; H, 5.20%; N, 8.48%; S, 8.23%; Ash, 9.62%
(3) Molecular weight: 250–600 upon an elution pattern of gel filtration
(4) U.V. spectrum (as shown in FIG. 1): Absorption maximum in an aqueous solution at 306 nm ($E_{1cm}^{1\%}=490$) shifted to 260 nm ($E_{1cm}^{1\%}=512$) in 0.01N HCl
(5) IR spectrum in KBr disc: as shown in FIG. 2
(6) NMR spectrum: 100 MHz NMR spectrum measured in D$_2$O by the use of DSS (sodium 2,2-dimethyl-2-silapentane-5-sulfonate) as an internal standard as shown in FIG. 3
(7) Solubility: Easily soluble in water, soluble in methanol and insoluble in ethyl acetate, chloroform, benzene
(8) Color reaction: Positive in iodine, potassium permanganate, slow bleaching in iodoplatinate, but negative in ninhydrin reaction
(9) Rf values on a thin layer chromatogram: Rf values of the substance No. 17927A$_2$ on various thin layer chromatograms are summarized in Table 4. Assay is made on a bioautogram using *Bacillus subtilis* PCI 219 as a test organism.

Table 4

| Solvents | Absorbent | Rf value | | |
|---|---|---|---|---|
| | | I* | II | III |
| n-butanol, isopropanol, water (7:7:6) | | 0.87 | 0.66 | |
| n-propanol, water (4:1) | | 0.85 | 0.57 | |
| isopropanol, water (7:3) | | 0.90 | | |
| n-butanol, methanol water (4:1:2) | | | | 0.39 |
| n-propanol, 0.1M phosphate buffer pH 7.0 (7:3) | | | | 0.42 |

I*: Eastman Chromagram Sheet 6064 (cellulose sheet)
II: Eastman Chromagram Sheet 6065 (cellulose sheet with fluorescent indicators)
III: Eastman Chromagram Sheet 6060 (silica gel sheet with fluorescent indicators)

(10) High voltage paper electrophoresis:
High voltage paper electrophoresis (55 volt/cm, 0.8 mA/cm) is effected by the use of "Toyo" filter paper No. 51A in 0.1M Tris-hydrochloric acid buffer (pH 7.5) and BPB (Bromophenol Blue) as a standard substance. Mobility of the standard substance is defined as 1.0 and that of the substance No. 17927A$_2$ is 0.75.
(11) Stability: The substance No. 17927A$_2$ is inactivated in its aqueous solution by 70% at 4° C. and pH 4.0 in 1 hour, by 20% at pH 5.0 in 7 hours and by 60% in 24 hours. Inactivation by not more than 5% is observed at pH 6.0 in 24 hours. 30% inactivation is observed at pH 9.0 in 24 hours. It is most stable at pH 7.0–8.0, but 20–25% inactivation at 27° C. is observed in 24 hours.
(12) Antibacterial spectrum: Minimum inhibitory concentrations (MIC) against various bacteria measured by an agar dilution method using heart infusion agar containing 1% glycerol are summarized in Table 5.

Table 5

| Test organism | | MIC (µg/ml) |
|---|---|---|
| *Staphylococcus aureus* FDA | 209P JC-1 | 0.39 |
| " | 396* (P) | 0.78 |
| *Micrococcus luteus* | PCI 1001 | 0.025 |
| *Bacillus subtilis* | PCI 219 | 0.05 |
| *Mycobacterium smegmatis* | ATCC 607 | >100 |
| *Escherichia coli* | NIHJ JC-2 | 0.2 |
| " | 609* (C,P) | 50 |
| " | 640* | 0.2 |
| " | 718* (P) | 0.2 |
| *Klebsiella pneumoniae* | 846* (C) | 0.39 |
| " | 847* (C) | 12.5 |
| *Enterobacter cloacae* | 971* (C,P) | 3.13 |
| *Proteus vulgaris* | OX-19 | 6.25 |
| " | 1415* (C,P) | 25 |
| *Proteus mirabilis* | 1332* (C,P) | 12.5 |
| *Proteus morganii* | 1510* (C,P) | 0.78 |
| *Proteus rettgeri* | 1603* (C) | 0.78 |
| *Proteus inconstans* | 1708* (C) | 6.25 |
| *Serratia marcescens* | 1853* (C,P) | 12.5 |
| *Pseudomonas aeruginosa* | SANK 73860 | 25 |
| " | 1046* (P) | >100 |

*Clinical isolate
In the above parentheses, C represents a strain resistant to cephalosporins and P represents a strain resistant to penicillins. The same definitions will be referred to hereinafter.

(13) Synergistic action: Synergistic action of the substance No. 17927A$_2$ having 0.23 µg/ml of I$_{50}$ (50% Inhibitory concentration) against β-lactamase produced from *Proteus morganii* with Cephaloridine or Ampicillin are summarized in Tables 6 and 7.

Table 6

| | MIC (µg/ml) | |
|---|---|---|
| Test organism | Cephaloridine alone | No. 17927A$_2$ coexisted 0.1 µg/ml |
| *Klebsiella penumoniae* 847 | 100 | 12.5 |
| *Proteus inconstans* 1708 | 1600 | 12.5 |

Table 7

| | MIC (µg/ml) | |
|---|---|---|
| Test organism | Ampicillin alone | No. 17927A$_2$ coexisted 0.1 µg/ml |
| *Escherichia coli* 640 | 25 | 1.56 |
| *Escherichia coli* 718 | 800 | 25 |
| *Proteus rettgeri* 1603 | 100 | 50 |

Figure 4:
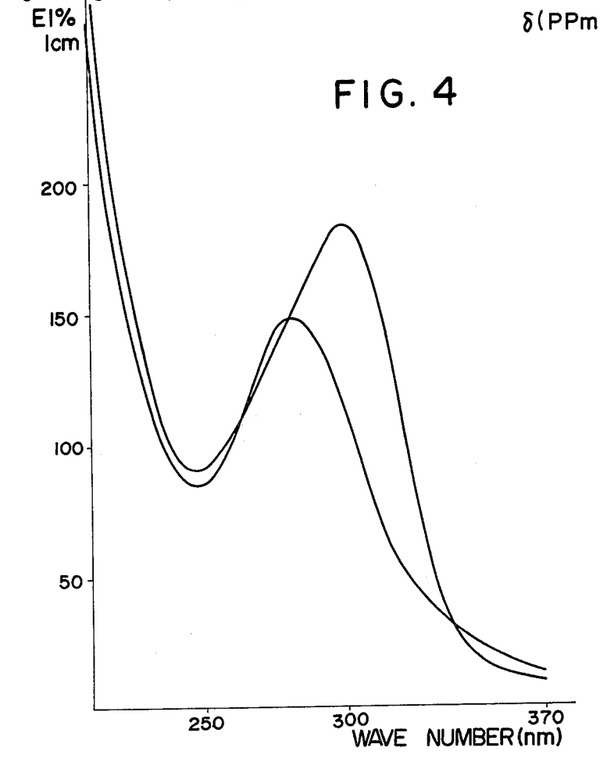
Figure 5:
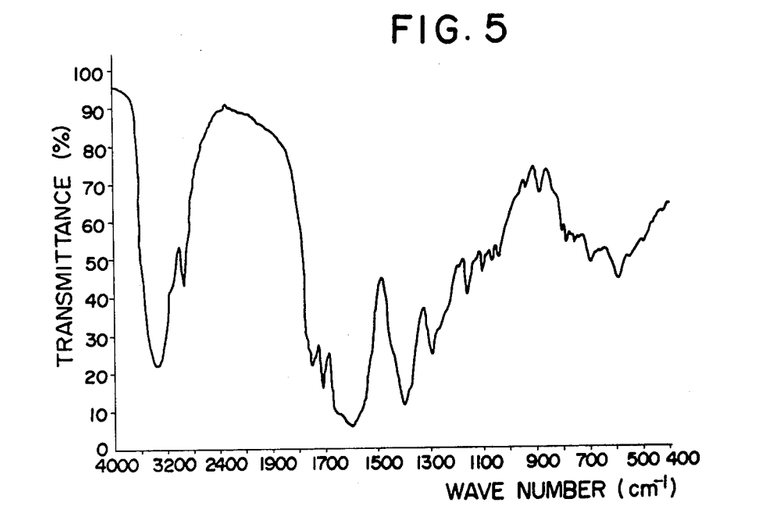
Figure 6:
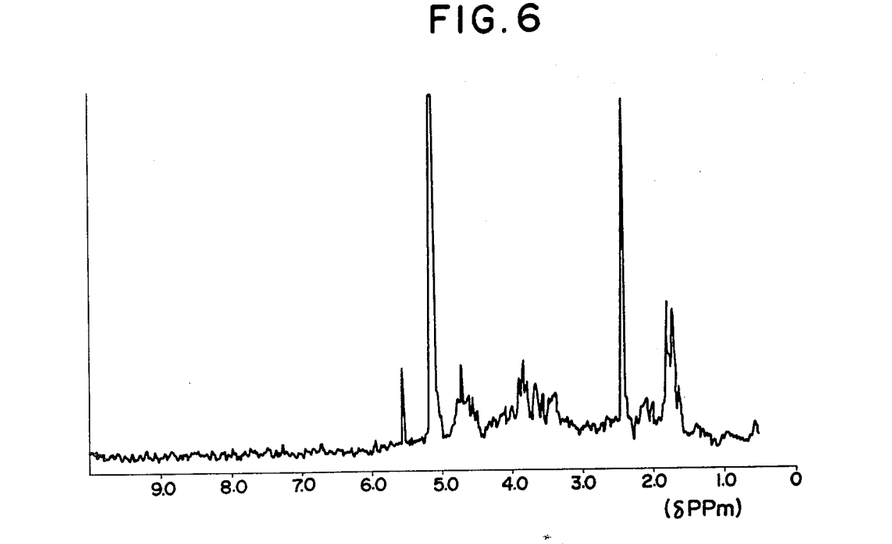

Substance No. 17927A$_1$ (1) Color and shape of the substance: Pale yellow powder when freeze-dried
(2) Analysis (Found): 1st analysis, C, 44.89%; H, 5.66%; N, 9.02%; S, 7.00%; Ash, 14.27%; 2nd analysis, C, 42.86%; H, 5.35%; N, 8.21%; S, 6.70%; Ash, 17.54%.
(3) Molecular weight: 250–600 upon an elution pattern of gel filtration
(4) U.V. spectrum (as shown in FIG. 4): Absorption maximum in an aqueous solution at 298 nm ($E_{1\ cm}^{1\%}=192$) shifted to 282 nm ($E_{1\ cm}^{1\%}=160$) in 0.01 N HCl
(5) IR spectrum: as shown in FIG. 5
(6) NMR spectrum: 100 MHz NMR spectrum measured in D$_2$O by the use of TMS (tetramethylsilane) as an external standard as shown in FIG. 6
(7) Solubility: Easily soluble in water, soluble in methanol and insoluble in ethyl acetate, chloroform, benzene (8) Color reaction: Positive in iodine, potassium permanganate, slow bleaching in iodoplatinate, but negative in ninhydrin reaction (9) Rf values on a thin layer chromatogram:
Rf values of the substance No. 17927A$_1$ on various thin layer chromatograms are summarized in Table 8. Assay is made on a bioautogram using *Bacillus subtilis* PCI 219 as a test organism.

Table 8

| Solvents | Adsorbent* I A$_1$ | II A$_1$ | III A$_1$ |
|---|---|---|---|
| n-butanol, isopropanol, water (7:7:6) | 0.86 | 0.56 | |
| n-propanol, water (4:1) | 0.80 | 0.45 | |
| isopropanol, water (7:3) | 0.87 | | |
| n-butanol, methanol, water (4:1:2) | | | 0.31 |
| n-propanol, 0.1M phosphate buffer pH 7.0 (7:3) | | | 0.37 |

*I: Eastman Chromagram Sheet 6064 (cellulose sheet)
II: Eastman Chromagram Sheet 6065 (cellulose sheet with fluorescent indicators)
III: Eastman Chromagram Sheet 6060 (silica gel sheet with fluorescent indicators)

(10) High voltage paper electrophoresis:
High voltage paper electrophoresis (55 volt/cm, 0.8 mA/cm) is effected by the use of "Toyo" filter paper No. 51A in 0.1 M Tris-hydrochloric acid buffer (pH 7.5) and BPB (Bromophenol Blue) as a standard substance. Mobility of the standard substance is defined as 1.0 and that of the substance No. 17927A$_1$ is 0.75.

(11) Stability: The substance No. 17927A$_1$ is inactivated in its aqueous solution by 70% at 4° C. and pH 4.0 in 1 hour, by 20% at oH 5.0 in 7 hours and by 60% in 24 hours. Inactivation by not more than 5% is observed at pH 6.0 in 24 hours. 30% inactivation is observed at pH 9.0 in 24 hours. It is most stable at pH 7.0–8.0, but 20–25% inactivation at 27° C. is observed in 24 hours.

(12) Antibacterial spectrum: Minimum inhibitory concentrations (MIC) against various bacteria are measured by an agar dilution method using Heart-infusion agar containing 1% glycerol summarized in Table 9.

Table 9

| Test organism | | MIC (µg/ml) |
|---|---|---|
| *Staphylococcus aureus* FDA | 209P JC-1 | 0.39 |
| " | 396* (P) | 0.78 |
| *Micrococcus luteus* | PCI 1001 | 0.05 |
| *Bacillus subtilis* | PCI 219 | 0.05 |
| *Mycobacterium smegmatis* | ATCC 607 | 50 |
| *Escherichia coli* | NIHJ JC-2 | 0.2 |
| " | 609* (C,P) | 0.2 |
| *Klebsiella pneumoniae* | 846* (C) | 0.39 |
| " | 847* (C) | 6.25 |
| *Enterobacter cloacae* | 971* (C,P) | 0.78 |
| *Proteus vulgaris* | OX-19 | 1.56 |
| " | 1415* (C,P) | 1.56 |
| *Proteus mirabilis* | 1332* (C,P) | 3.13 |
| *Proteus morganii* | 1510* (C,P) | 1.56 |
| *Proteus rettgeri* | 1603* (C) | 1.56 |
| *Proteus inconstans* | 1708* (C) | 1.56 |
| *Serratia marcescens* | 1853* (C,P) | 6.25 |
| *Pseudomonas aeruginosa* | SANK 73860 | 6.25 |
| " | 1046* (P) | >100 |

*Clinical isolate
In the above parentheses, C represents a strain resistant to cephalosporins and P represents a strain resistant to penicillins.

(13) Synergistic action: Synergistic action of the substance No. 17927A$_1$ having 0.27 µg/ml of I$_{50}$ (50% Inhibitory concentration) against β-lactamase produced from *Proteus morganii* with Cephaloridine are summarized in Table 10.

Table 10

| | MIC (µg/ml) | | |
|---|---|---|---|
| | Cephaloridine | No. 17927A$_1$ coexisted | |
| Test organism | alone | 0.1 µg/ml | 0.4 µg/ml |
| *Escherichia coli* 609 | 100 | 100 | 50 |
| *Klebsiella pneumoniae* 847 | 100 | 12.5 | 12.5 |
| *Proteus mirabilis* 1332 | 100 | 50 | 50 |
| *Proteus morganii* 1510 | 1600 | 50 | 50 |
| *Proteus inconstans* 1708 | 1600 | 6.25 | 3.13 |
| *Proteus rettgeri* 1603 | 1600 | 50 | 25 |

The salts of the substance No. 17927A$_2$ or substance No. 17927A$_1$ which may be employed as an antibiotic substance are medicinally, veterinarily or agriculturally-acceptable salts, preferably such pharmaceutically-acceptable salts as sodium, potassium, calcium, magnesium, aluminum or ammonium salt and most preferably sodium or potassium salt.

The substance No. 17927A$_2$ or No. 17927A$_1$ or salts thereof may be formulated into a pharmaceutical preparation for the prevention and treatment of bacterial infectious diseases and may be applied in such conventional dosage forms as tablets, capsules, injectable preparations, ointments, suppositories or sprayable preparations. For the treatment of human infectious diseases, they can be orally or parenterally administered, in general, in a dose of about 2–500 mg/Kg/day, preferably 5–100 mg/Kg/day in suitably divided dosage forms, for example, three or four times per day.

The substance No. 17927A$_2$ or No. 17927A$_1$ or salts thereof may be incorporated alone into the pharmaceutical preparation or in combination with other therapeutic agents, for instance, β-lactam antibiotic substances, e.g., Ampicillin, Amoxicillin, Carbenicillin, Benzylpenicillin, Cephaloridine, Cephalothin, Cephalexin, Cefazolin etc. or aminoglucoside antibiotic substances, e.g., Gentamicin etc.

This invention will be more fully illustrated by the following examples which are given for illustration purposes solely and not limiting the scope of this invention.

EXAMPLE 1

(a) To 100 ml of the under-mentioned medium A contained in a 500 ml-volume Sakaguchi flask was inoculated one loopful of *Streptomyces fulvoviridis* No. 17927 strain and then shaken culture was conducted at 27° C. for 72 hours with 120 strokes/min.

| Medium A | (w/v%) |
|---|---|
| Glycerol | 2.5 |
| Glucose | 0.5 |
| Yeast (press) | 1.0 |
| Soybean meal | 1.0 |
| Corn steep liquor | 1.0 |
| Calcium carbonate | 0.3 |
| KH$_2$PO$_4$ | 1.0 |
| "Disfoam" CB-442 (available from Nippon Oils and Fats Co., Ltd., Japan) | 0.01 |
| Solution in 100 ml of water of each 100 mg portion of FeSO$_4$ · 7H$_2$O. | 0.1 |

| Medium A | (w/v%) |
|---|---|
| $ZnSO_4 \cdot 7H_2O$ and $MnCl_2 \cdot 4H_2O$ | |
| pH (before sterilization) | 7.2 |

10 ml of this seed cultured broth were inoculated to 500 ml of the above-mentioned medium A contained in a 2 l-volume Erlenmeyer flask and cultivation was conducted at 28° C. and 220 rpm for 24 hours on a rotary shaker.

Each 500 ml portion of this second seed cultured broth was inoculated to two 30 l-volume jar-fermentors, each containing 15 l. of the medium A, and then cultivation was effected at 27° C. with an aeration of 15 l/min., an inner pressure of 0.5 Kg/cm$^2$ and an agitation of 220 rpm for 90 hours to produce a cultured broth containing the substance No. 17927A$_2$ at 2 units/ml and the substance No. 17927A$_1$ at 2 units/ml.

The cultured broth was filtered with 10 w/v % Celite and 20 l. of the filtrate thus obtained were cooled to 4° C., adjusted to pH 7.5 and adsorbed on a column of 3 l. of Diaion HP-20 at a flow rate of 240 ml/min., which was then eluted with a cold deionized water containing 10% acetone. From the eluates were collected 2.5 l. of active fractions, which were then adjusted to pH 7.5 and the acetone was removed by evaporation and the residue was concentrated to 500 ml. The concentrate was freeze-dried to afford 50 g of a brown powder having an activity of 0.5 unit/mg.

Then, 40 g of the powder were dissolved in 1.5 l. of a deionized water and, after adjusting its pH to 7.5, was adsorbed on a column (10×20 cm) of 1.5·l. of DEAE-Sephadex A-25 equilibrated with 0.01 M phosphate buffer (pH 7.5) at 4° C. at a flow rate of 50 ml/min. and developed and eluted with the same buffer to collect each 450 ml. portion of fractions.

(b) The substance No. 17927A$_1$ was eluted into fractions No. 6 through No. 18.

A total of 4.6 l. of the active fractions from fraction No. 8 to fraction No. 17 inclusive was adjusted to pH 7.5, adsorbed on a column of 800 ml of active carbon, which was washed with 4 l. of a deionized water and the absorbates were eluted with a 8% cold aqueous acetone at a flow rate of 25 ml/min. Each 400 ml portion of fractions was taken to collect active fractions No. 3 to 6, which were then adjusted its pH to 7.5, concentrated and freeze-dried to give 1.0 g of a pale brown powder having an activity of 5 units/mg.

A solution of 1 g of this powder in 50 ml of a deionized water was extracted with 100 ml of a 1% methylene chloride solution of dimethyl benzyl cetyl ammonium chloride. The solvent layer was extracted with 50 ml of a cold 0.5% aqueous solution of sodium chloride. The aqueous layer was washed with 50 ml of methylene chloride, a small volume of the solvent was removed by evaporation and the residue was adsorbed on a column of 200 ml of Diaion HP-20 at 4° C., which was then developed and eluted with a deionized water to give the substance No. 17927A$_1$. Active fractions were collected and freeze-dried to afford 66 mg of a pale brown powder having an activity of 15 units/mg.

(c) On the other hand, the substance No. 17927A$_2$ was eluted into fractions No. 19 through No. 30 inclusive by the above-mentioned column chromatography or DEAE-Sephadex A-25. A total of 4.6 l. of active fractions from fraction No. 21 to fraction No. 30 inclusive was adjusted to pH 7.5, adsorbed on a column of 800 ml of active carbon, which was washed with 4 l. of a deionized water and eluted with a cold 8% aqueous acetone at a flow rate of 25 ml/min. Each 400 ml portion of fractions was taken to collect active fractions No. 3 to 6, which were then adjusted to pH 7.5, concentrated and freeze-dried to give 1.0 g of a pale brown powder having an activity of 1.5 units/mg.

A solution of 1 g of this powder in 50 ml of a deionized water was extracted with 100 ml of a 1% (w/v) methylene chloride solution of dimethyl benzyl cetyl ammonium chloride. The solvent layer was extracted with 50 ml of a cold 0.5% aqueous solution of sodium chloride. The aqueous layer was washed with 50 ml of methylene chloride, a small volume of the solvent was removed by evaporation and the residue was adsorbed on a column of 200 ml of Diaion HP-20 at 4° C., which was then developed and eluted with a deionized water to give the substance No. 17927A$_2$. Active fractions were collected and freeze-dried to afford 23 mg of the substance No. 17927A$_2$ as a pale brown powder having an activity of 13 units/mg.

EXAMPLE 2

One loopful of *Streptomyces fulvoviridis* No. 17927 strain was inoculated to 100 ml of the under-mentioned medium B contained in a 500 ml-volume Sakaguchi flask and cultivation was effected at 27° C. for 72 hours on a reciprocating shaker (120 strokes/min.). The cultured broth (10 ml) was inoculated to 500 ml of the meidum B contained in a 2 l-volume Erlenmeyer flask and shaken culture was further done on a rotary shaker at 27° C. for 24 hours (220 rpm).

| Medium B | (w/v%) |
|---|---|
| Glycerol | 2.5 |
| Glucose | 0.5 |
| Yeast (press) | 1.0 |
| Soybean meal | 2.0 |
| Calcium carbonate | 0.3 |
| $KH_2PO_4$ | 1.0 |
| "Disfoam" CB-442 | 0.01 |
| Solution in 100 ml of water of each 100 mg portion of $FeSO_4 \cdot 7H_2O$, $ZnSO_4 \cdot 7H_2O$ and $MnCl_2 \cdot 4H_2O$ | 0.1 |
| pH (before sterilization) | 7.2 |

Each 1.2 l. portion of this seed culture was inoculated to two 30 l-volume jar-fermentors, each containing 15 l. of the medium B, and cultivation was effected at 27° C. with an aeration of 40 l/min., an inner pressure of 0.5 Kg/cm$^2$ and an agitation of 200–400 rpm for 65 hours. The cultured broth was filtered with 3 Kg of Celite and the resulting filtrate (21 l.) was cooled to 10° C., adjusted to pH 7.0 and passed through a column (10×42 cm) of 3.3 l. of Amberlite XAD-2 at a flow rate of 250 ml/min., which was then washed with 12 l. of a cold deionized water. Effluents and wash fractions were combined and the active substance was adsorbed on a column (10×20 cm) of 1.5 l. of active carbon for chromatography, which was then washed with 10 l. of 0.05 M ammonium formate and eluted with a deionized water containing 8% acetone at a flow rate of 25 ml/min. Each 2 l. portion of fractions was taken and fractions No. 2 and No. 3 showed an antibacterial activity. From 4 l. of the active fraction was distilled off the acetone and the residue was concentrated, adjusted to pH 7.5 and freeze-dried to leave 39.45 g of a brown powder containing sodium salt of the substance No. 17927A$_2$ and sodium salt of the substance No. 17927A$_1$ having an activity of 1.0 unit/mg.

EXAMPLE 3

A solution of 1 g of the powder obtained in the above Example 2 in 100 ml of a deionized water was adjusted to pH 7.5 with dilute sodium hydroxide and adsorbed on a column (0.8×10 cm) of 5 ml of Dowex 21K (CH$_3$COO$^-$ form) at a flow rate of 0.3 ml/min., which was then washed with 30 ml of a deionized water and eluted with 0.2 M aqueous sodium chloride to collect each 15 ml portion of fractions. The active substance was contained in fractions No. 12 through No. 29. 270 ml of the pooled active fractions were diluted to 360 ml with a deionized water, adjusted to pH 7.0 with dilute sodium hydroxide and adsorbed on a column (1.0×9.5 cm) of QAE-Sephadex equilibrated with 0.02 M phosphate buffer (pH 7.0) at a flow rate of 1.5 ml/min., which was then developed and eluted with 0.05 M phosphate buffer (pH 7.0) containing 0.5 M sodium chloride at the same flow rate. Each 5 ml fraction was taken and the active substance was contained in fractions No. 7 through No. 15. The so obtained eluate was adjusted to pH 7.5 and adsorbed on a column prepared from 2 g of active carbon for chromatography, which was then washed with a deionized water and the active substance was eluted from 30 ml of 10% aqueous acetone and the eluate was concentrated under reduced pressure to 10 ml. The concentrate was adjusted to pH 7.5 with dilute sodium hydroxide and adsorbed on a column (1.5×5.6 cm) of 10 ml of Amberlite IRA-68 (Cl$^-$ form), which was then washed with 30 ml of a deionized water and eluted with 0.2 M aqueous sodium chloride. The eluates were fractionated to each 15 ml fractions. Fractions No. 8 through No. 16 showed an antibacterial activity and they were combined and again adsorbed on a column of 1 g of active carbon, which was then washed with water and eluted with 30 ml of 8% aqueous acetone. The eluate was concentrated under reduced pressure to 10 ml and the concentrate was freeze-dried to afford 10 mg of a pale brown powder of an activity of 30 units/mg containing sodium salt of the substance No. 17927A$_2$ and sodium salt of the substance No. 17927A$_1$.

EXAMPLE 4

A solution of 2 g of the powder obtained in the above Example 2 in 120 ml of a deionized water was adjusted to pH 7.5 with dilute sodium hydroxide and adsorbed on a column of 20 ml of Duolite A-4 (Cl$^-$ form) at a flow rate of 1 ml/min., which was then washed with 100 ml of a deionized water and eluted with 0.3 M aqueous sodium chloride to collect fractions in each 10 ml portion. The active substance was eluted in fractions No. 3 through No. 9. 140 ml of the active fractions were diluted to 300 ml with a deionized water, the resulting solution was adjusted to pH 7.0 and purified by QAE-Sephadex column in the same manner as in Example 3, elution from an active carbon column and freeze-drying to give 33 mg of a powder of an activity of 30 units/mg containing sodium salt of the substance No. 17927A$_2$ and sodium salt of the substance No. 17927A$_1$.

EXAMPLE 5

(a) A solution of 3.0 g of the powder obtained in the above Example 2 in 3.5 l. of a deionized water was adsorbed on a column (10.5×16 cm) of DEAE-Sephadex A-25 equilibrated with 0.01 M phosphate buffer (pH 7.5) at a flow rate of 50 ml/min. Subsequently, elution was carried out with the same buffer at the same flow rate to collect fractions in each 430 ml portion.

(b) The active substance, substance No. 17927A$_1$, was contained in fractions No. 7 through No. 19. Active fractions No. 8 through No. 17 were collected to amount to 4.6 l. They were adsorbed on a column (5×10 cm), which was prepared from the active carbon for chromatography treated with 0.1 N hydrochloric acid and washed with a deionized water until no Cl$^-$ ion was detected, at a flow rate of 53 ml/min. The column was then washed with 4 l. of a deionized water and eluted with 8% aqueous acetone at a flow rate of 13 ml/min. Fractions were taken in each 430 ml portion and the active substance was eluted in fractions No. 3 through No. 7. 2150 ml of the active fraction were adjusted its pH to 7.5 with dilute aqueous sodium hydroxide, concentrated to 100 ml, again adjusted to pH 7.5 and freeze-dried to afford 1.57 g of sodium salt of the substance No. 17927A$_1$ as a pale yellow powder of 10 units/mg.

160 mg of the powder was dissolved in a small amount of a deionized water was admixed with 1 g of Avicel and freeze-dried. The resulting product was layered on the top of column (1.0×25 cm) prepared from 10 g of Avicel equilibrated with 90% acetonitrile, which was then eluted with the same solvent, whereby the active substance was eluted into fractions No. 22 through No. 29. Fractions No. 25 to No. 27 inclusive were collected, concentrated under reduced pressure, adjusted its pH to 7.5 and freeze-dried to give 6 mg of sodium salt of the substance No. 17927A$_1$ having an activity of 200 units/mg.

(C) On the other hand, the substance No. 17927A$_2$ was contained in fractions No. 22 through No. 29. Active fractions No. 23 through No. 28 were collected to amount to 2.6 l. They were adsorbed on a column (5×10 cm), which was prepared from the active carbon for chromatography treated with 0.1 N hydrochloric acid and washed with a deionized water until no Cl$^-$ ion was detected, at a flow rate of 13 ml/min. The column was then washed with 1 l. of a deionized water and eluted with 8% aqueous acetone at a flow rate of 4 ml/min. Fractions were taken in each 75 ml portion and the active substance was contained in fractions No. 3 through No. 7. 375 ml of the active fraction were adjusted to pH 7.5 with dilute aqueous sodium hydroxide, concentrated to 100 ml, again adjusted to pH 7.5 and freeze-dried to afford 947 mg of sodium salt of the substance No. 17927A$_2$ as a pale yellow powder of 6 units/mg.

140 mg of the powder was dissolved in a small amount of a deionized water was admixed with 1 g of Avicel and freeze-dried. The resulting product was applied on a column (1.0×25 cm) prepared from 15 g of Avicel equilibrated with 90% acetonitrile, which was then eluted with the same solvent, whereby the active substance was eluted into fractions No. 12 through No. 24. Fractions No. 13 to No. 23 inclusive were collected, concentrated under reduced pressure, adjusted to pH 7.5 and freeze-dried to give 2.5 mg of sodium salt of the substance No. 17927A$_2$ having an activity of 200 units/mg.

EXAMPLE 6

(a) One loopful of *Streptomyces fulvoviridis* No. 17927 strain from slant was inoculated to 100 ml of the above-mentioned medium B in a 500 ml-volume flask and cultivation was made at 27° C. for 72 hours on a reciprocating shaker. 10 ml of the first seed cultured broth were inoculated to 500 ml of the medium B in a 2 l-volume Erlenmeyer flask and cultivation was effected at 27° C. for 24 hours on a rotary shaker at 220 rpm. 1.2 l of the second seed cultured broth were inoculated to 40 l. of the medium B in a 100 l-volume fermentor and cultivation was made at 27° C. for 24 hours with an aeration of 40 l/min., an inner pressure of 0.5 Kg/cm$^2$ and an agitation of 100-300 rpm.

Thereafter, each 9 l. portion of the third seed cultured broth was inoculated to two 600 l-volume fermentors, each containing 300 l. of the medium B. Cultivation was conducted at 27° C. for 89 hours with an aeration of 300 l/min., an inner pressure of 0.5 Kg/cm$^2$ and an agitation of 100-300 rpm.

To 680 l. of the cultured broth were added 54 Kg of Celite and filtration was done with a filter press to leave 550 l. of the cultured broth filtrate, whose antibacterial activity was 4 units/ml. The filtrate was immediately cooled to 4° C., adjusted its pH to 7.0 and passed through a column (32×93 cm) of 75 l. of Amberlite XAD-2 at a flow rate of 4.7 l/min. The column was washed with 200 l. of a deionized water, the effluents and wash fractions were combined and adsorbed on a column (31×46 cm) of 35 l. of active carbon for chromatography treated with 0.1 N hydrochloric acid at a flow rate of 2.33 l/min. The column was washed with 200 l. of 0.05 M ammonium formate and then eluted with a deionized water containing 10% acetone at a flow rate of 580 ml/min. Eluates were fractionated in each 50 l. portion. Fractions No. 2 through No. 5 contained the active substance. 200 l. of the active fractions thus taken were adjusted to pH 7.0 and the acetone was distilled off under reduced pressure and concentrated to leave 95 l. of the concentrate whose activity was 9.9 units/ml. The concentrate was cooled to 10° C., adjusted to pH 7.1 with dilute sodium hydroxide and adsorbed on a column (32×125 cm) of 100 l. of Diaion HP-20 at a flow rate of 1.7 l/min., which was then eluted with a deionized water at 10° C. at the same flow rate and eluates were fractionated in each 10 l. portion.

Eluted fractions No. 22 through No. 31 inclusive contained the substances No. 17927A$_2$ and No. 17927A$_1$. At this stage, another active fraction named the substance No. 17927C was eluted into fractions No. 17 to 19 and these fractions (30 l.) were observed to contain 2.2 units/ml of the said substance C. This substance C is an antibiotic substance having a relative mobility of 1.3 to BPB in the above-depicted high voltage paper electrophoresis and a β-lactamase inhibition activity as seen in the substances A$_1$ and A$_2$, but the main components thereof, the substances C$_1$ and C$_2$, have been identified with MM 13902 disclosed in Japanese Patent Provisional Publication No. 14692/1975 and MM 17880 disclosed in Japanese Patent Provisional Publication No. 11870/1976, respectively.

The active fraction containing the substances No. 17927A$_2$ and No. 17927A$_1$ eluted as fractions No. 22 through No. 31 inclusive was concentrated to leave 81 l. of the concentrate having an activity of 10 units/ml and 7.5 units/ml, respectively.

The concentrate was adsorbed on a column (31×30 cm) of 22 l. of DEAE-Sephadex A-25 previously equilibrated with 0.01 M sodium phosphate buffer (pH 7.5) at a flow rate of 660 ml/min. and then the column was eluted with the cooled buffer of the same composition at the same flow rate to take fractions in each about 5 l. portion.

(b) The active fraction containing the substance No. 17927A$_1$ eluted to fractions No. 22 through No. 31 inclusive was concentrated to leave 81 l. of the concentrate having an activity of 10 units/ml. 10 ml. of the concentrate were freeze-dried to yield the substance No. 17927A$_1$ having an activity of 7.5 units/mg.

The concentrate was adsorbed on a column (31×30 cm) of 22 l. of DEAE-Sephadex A-25 previously equilibrated with 0.01 M sodium phosphate buffer (pH 7.5) at a flow rate of 660 ml/min. and then the column was eluted with the cooled buffer of the same composition at the same flow rate to take fractions in each about 5 l. portion. The active substance was eluted into fractions No. 18-27. Fractions No. 19 through No. 25 inclusive were collected to amount to 40 l. of the active fraction, whose activity was 13.2 units/ml.

The eluate was concentrated to 9 l. under reduced pressure and adsorbed on a column (25×61 cm) of 30 l. of Diaion HP-20 at a flow rate of 500 ml/min., which was then eluted with a deionized water at the same flow rate. A concentration of the phosphate in the eluate was measured by determination of conductivity (using an instrument available from Yanagimoto Shoji K. K., Japan). The inorganic salt was detected at fraction No. 5 as a peak between fraction No. 3 and No. 9, while the active substance was eluted into fractions No. 13 through No. 24 with fractions No. 16 and No. 17 as a peak. Fractions No. 15 through No. 23 inclusive were collected to afford 18 l. of the active fraction.

This active fraction was concentrated to 450 ml under reduced pressure, adjusted to pH 7.5 with dilute sodium hydroxide and freeze-dried to produce 7 g of sodium salt of the substance No. 17927A$_1$ having an activity of 63 units/mg. A solution of 1 g of the product in 4 ml of water was adjusted its pH to 7.5, 8 g of Avicel were portionwise added thereto and blended for sufficient homogeneity and then 36 ml of acetonitrile were added thereto to form a homogeneous suspension. The suspension was placed on the top of a column (3.4×22 cm) containing 80 g of Avicel previously equilibrated with acetonitrile containing 10% water and, after well settlement, development of the column was initiated. Immediately before the initial acetonitrile containing 10% water disappeared at the top of the column, fresh prepared acetonitrile containing 10% water was placed and development and elution were continued at a flow rate of 5 ml/min. Eluates were fractionated in each 20 ml portion, the active fractions No. 88 through No. 113 inclusive were collected and concentrated to 20 ml under reduced pressure. The concentrate was adjusted its pH to 7.5 with dilute sodium hydroxide and the whole volume was adsorbed on a column (4.3×70 cm) of 1 l. of Biogel P-2, which was then developed with a deionized water at a flow rate of 1.6 ml/min. The active substance was eluted into fractions No. 28-50, each being 15 ml, and active fractions No. 38 through No. 44 inclusive were collected, adjusted to pH 7.5 and freeze-dried to afford 32.9 mg of sodium salt of the substance No. 17927A$_1$ having an activity of 1300 units/mg as a pale yellow powder. The pure sample thereof exhibited the absorption maximum at 298 nm in its ultraviolet absorption spectrum in aqueous solution and $E_{1cm}^{1\%}$ was 119.

Further, the column chromatography on Biogel P-2 was repeated to yield 15.6 mg of sodium salt of the substance No. 17927A$_1$ having an activity of 2185 units/mg as a powder. This further purified sample showed the absorption maximum at 298 nm in its ultraviolet absorption spectrum in aqueous solution and $E_{1cm}^{1\%}$ was 192.

(C) On the other hand, the substance No. 17927A$_2$ was eluted into fractions No. 32–40. Fractions No. 33 through No. 39 inclusive were collected to amount to 44 l. of the active fraction, whose activity was 2.8 units/ml.

The eluate was concentrated to 9 l. under reduced pressure and adsorbed on a column (25×61 cm) of 30 l. of Diaion HP-20 at a flow rate of 500 ml/min., which was then eluted with a deionized water at the same flow rate. A concentration of the phosphate in the eluate was measured by determination of electro conductivity (using an instrument available from Yanagimoto Shoji K. K., Japan). The phosphate was detected in fraction No. 5 as a peak between fraction No. 3 and No. 9, while the active substance was eluted into fractions No. 16 through No. 30 with fraction No 17 as a peak. Fractions No. 16 through No. 30 inclusive were collected to afford 30 l. of the active fraction.

This active fraction was concentrated to 450 ml under reduced pressure, adjusted its pH to 7.5 with dilute sodium hydroxide and freeze-dried to produce 4 g of sodium salt of the substance No. 17927A$_2$ having an activity of 30 units/mg. A solution of 1.2 g of the product in 2.5 ml of water was adjusted its pH to 8.0, 5 g of Avicel were portionwise added thereto and blended for sufficient homogenity and then 22.5 ml of acetonitrile were added thereto to form a homogenous suspension. The suspension was placed on the top of a column (2.6×18.5 cm) containing 40 g of Avicel previously equilibrated with acetonitrile containing 5% water and, after well settlement, development of the column was started. Immediately before the initial acetonitrile containing 10% water disappeared at the top of the column, fresh prepared acetonitrile containing 10% water was placed and development and elution were continued at a flow rate of 5 ml/min. Eluates were fractionated in each 20 ml portion, the active fractions No. 31 through No. 40 inclusive were collected and concentrated to 20 ml under reduced pressure. The concentrate was adjusted its pH to 7.5 with dilute sodium hydroxide and the whole volume was adsorbed on a column (4.3×70 cm) of 1 l. of Biogel P-2, which was then developed with a deionized water at a flow rate of 1.6 ml/min. The active substance was eluted into fractions No. 25–41, each being 15 ml, and active fractions No. 30 through No. 38 inclusive were collected, adjusted its pH to 7.5 and freeze-dried to afford 21.3 mg of sodium salt of the substance No. 17927A$_2$ having an activity of 1470 units/mg as a pale yellow powder. The pure sample thereof exhibited the absorption maximum at 306 nm in its ultraviolet absorption spectrum in aqueous solution and $E_{1cm}^{1\%}$ was 330.

Further, the column chromatography on Biogel P-2 was repeated to yield 10.5 mg of sodium salt of the substance No. 17927A$_2$ having an activity of 2350 units/mg as a powder. This further purified sample exhibited the absorption maximum at 306 nm in its ultraviolet absorption spectrum in aqueous solution and $D_{1cm}^{1\%}$ was 490.

What is claimed is:

1. As a composition of matter, a substance No. 17927A$_2$ and a pharmaceutically-acceptable salt thereof, its sodium salt having the following properties;
   (1) Color and shape of the substance: Pale yellow powder when freeze-dried
   (2) Analysis (Found): C, 46.52%; H, 5.20%; N, 8.48%; S, 8.23%; Ash, 9.62%
   (3) Molecular weight: 250–600 upon an elution pattern of gel filtration
   (4) U.V. spectrum (as shown in FIG. 1): Absorption maximum in an aqueous solution at 306 nm ($E_{1cm}^{1\%}=490$) shifted to 260 nm ($E_{1cm}^{1\%}=512$) in 0.01 N HCl
   (5) IR spectrum in KBr disc: as shown in FIG. 2
   (6) NMR spectrum: 100 MHz NMR spectrum measured in D$_2$O by the use of DSS (sodium 2,2-dimethyl-2-silapentane-5-sulfonate) as an internal standard as shown in FIG. 3
   (7) Solubility: Easily soluble in water, soluble in methanol and insoluble in ethyl acetate, chloroform, benzene
   (8) Color reaction: Positive in iodine, potassium permanganate, slow bleaching in iodoplatinate, but negative in ninhydrin reaction
   (9) Antibacterial activity: Broad antibacterial activity against gram-positive and gram-negative bacteria including *Staphylococcus aureus, Bacillus subtilis, Escherichia coli, Klebsiella pneumonie, Proteus vulgaris, Proteus mirabilis, Proteus rettgeri, Enterobacter cloacae* and *Serratia marcescens*
   (10) Synergistic effect: Inhibitory action of β-lactamase and synergistic effect by the combined use of penicillin-type or cephalosporin-type antibiotic substances ineffective against resistant strains producing β-lactamase.

2. A composition of matter according to claim 1 wherein said pharmaceutically-acceptable salt is sodium or potassium salt.

3. As a composition of matter, a substance No. b 17927A$_1$ and a pharmaceutically-acceptable salt thereof, its sodium salt having the following properties:
   (1) Color and shape of the substance: Pale yellow powder then freeze-dried
   (2) Analysis (Found): 1st analysis; C, 44.89%; H, 5.66%; N, 9.02%; S, 7.00%; Ash, 14.27%; 2nd analysis; C, 42.86%; H, 5.35%; N, 8.21%; S, 6.70%; Ash, 17.54%.
   (3) Molecular weight: 250–600 upon an elution pattern of gel filtration
   (4) U.V. spectrum (as shown in FIG. 4): Absorption maximum in an aqueous solution at 298 nm ($E_{1cm}^{1\%}=192$) shifted to 282 nm ($E_{1cm}^{1\%}=160$) in 0.01 N HCl
   (5) IR spectrum in KBr disc: as shown in FIG. 5
   (6) NMR spectrum: 100 MHz NMR spectrum measured in D$_2$O by the use of TMS (tetramethylsilane) as an external standard as shown in FIG. 6
   (7) Solubility: Easily soluble in water, soluble in methanol and insoluble in ethyl acetate, chloroform, benzene
   (8) Color reaction: Positive in iodine, potassium permanganate, slow bleaching in iodoplatinate, but negative in ninhydrin reaction
   (9) Antibacterial activity: Broad antibacterial activity against gram-positive and gram-negative bacteria including *Staphylococcus aureus, Bacillus subtilis, Escherichia coli, Klebsiella pneumonie, Proteus vul-*

*garis, Proteus mirabilis, Proteus rettgeri, Enterobacter cloacae* and *Serratia marcescens*

(10) Synergistic effect: Inhibitory action of β-lactamase and synergistic effect by the combined use of penicillin-type or cephalosporin-type antibiotic substances ineffective against resistant strains producing β-lactamase.

4. A composition of matter according to claim 3 wherein said pharmaceutically-acceptable salt is sodium or potassium salt.

5. A process for the production of antibiotic substances, substance No. 17927A$_1$ and substance No. 17927A$_2$, which comprises cultivating a substances No. 17927A$_1$ and No. 17927A$_2$-producing microorganism belonging to the genus Streptomyces, isolating said substances No. 17927A$_1$ and No. 17927A$_2$ from a cultured broth and separating said substance No. 17927A$_1$ from said substance No. 17927A$_2$; sodium salt of said substance No. 17927A$_1$ having the following properties;

(1) Color and shape of the substance: Pale yellow powder when freeze-dried (2) Analysis (Found): 1st analysis; C, 44.89%; H, 5.66%; N, 9.02%; S, 7.00%; Ash, 14.27%; 2nd analysis; C, 42.86%; H, 5.35%; N, 8.21%; S, 6.70%; Ash, 17.54%.

(3) Molecular weight: 250–600 upon an elution pattern of gel filtration (4) U.V. spectrum (as shown in FIG. 4): Absorption maximum in an aqueous solution at 298 nm ($E_{1cm}^{1\%}=192$) shifted to 282 nm ($E_{1cm}^{1\%}=160$) in 0.01 N HCl (5) IR spectrum in KBr disc: as shown in FIG. 5

(6) NMR spectrum: 100 MHz NMR spectrum measured in D$_2$O by the use of TMS (tetramethylsilane) as an external standard as shown in FIG. 6

(7) Solubility: Easily soluble in water, soluble in methanol and insoluble in ethyl acetate, chloroform, benzene (8) Color reaction: Positive in iodine, potassium permanganate, slow bleaching in iodoplatinate, but negative in ninhydrin reaction (9) Antibacterial activity: Broad antibacterial activity against gram-positive and gram-negative bacteria including *Staphylococcus aureus, Bacillus subtilis, Escherichia coli, Klebsiella pneumonie, Proteus vulgaris, Proteus mirabilis, Proteus rettgeri, Enterobacter cloacae* and *Serratia marcescens*

(10) Synergistic effect: Inhibitory action of β-lactamase and synergistic effect by the combined use of penicillin-type or cephalosporin-type antibiotic substances ineffective against resistant strains producing β-lactamase and sodium salt of said substance No. 17927A$_2$ having the following properties;

(1) Color and shape of the substance: Pale yellow powder when freeze-dried (2) Analysis (Found): C, 46.52%; H, 5.20%; N, 8.48%; S, 8.23%; Ash, 9.62%

(3) Molecular weight: 250–600 upon an elution pattern of gel filtration (4) U.V. spectrum (as shown in FIG. 1): Absorption maximum in an aqueous solution at 306 nm ($E_{1cm}^{1\%}=490$) shifted to 260 nm ($E_{1cm}^{1\%}=512$) in 0.01 N HCl (5) IR spectrum in KBr disc: as shown in FIG. 2

(6) NMR spectrum: 100 MHz NMR spectrum measured in D$_2$O by the use of DSS (sodium 2,2-dimethyl-2-silapentane-5-sulfonate) as an internal standard as shown in FIG. 3

(7) Solubility: Easily soluble in water, soluble in methanol and insoluble in ethyl acetate, chloroform, benzene (8) Color reaction: Positive in iodine, potassium permanganate, slow bleaching in iodoplatinate, but negative in ninhydrin reaction (9) Antibacterial activity: Broad antibacterial activity against gram-positive and gram-negative bacteria including *Staphylococcus aureus, Bacillus subtilis, Escherichia coli, Klebsiella pneumonie, Proteus vulgaris, Proteus mirabilis, Proteus rettgeri, Enterobacter cloacae* and *Serratia marcescens*

(10) Synergistic effect: Inhibitory action of β-lactamase and synergistic effect by the combined use of penicillin-type or cephalosporin-type antibiotic substances ineffective against resistant strains producing β-lactamase.

6. A process for the production according to claim 5 wherein said substances No. 17927A$_1$ and No. 17927A$_2$-producing microorganism belonging to the genus Streptomyces is *Streptomyces fulvoviridis, Streptomyces olivaceus* or *Streptomyces argenteolus.*

7. A process for the production according to claim 5 wherein said substances No. 17927A$_1$ and No. 17927A$_2$-producing microorganism belonging to the genus Streptomyces is *Streptomyces fulvoviridis* ATCC 15863, *Streptomyces fulvoviridis* strain No. 17927 (Ferm-No. 3935), *Streptomyces fulvoviridis* strain No. 18032 (Ferm-No. 3936), *Streptomyces fulvoviridis* strain No. 18333 (Ferm-No. 3937), *Streptomyces olivaceus* ATCC 21379, *Streptomyces olivaceus* ATCC 31126 or *Streptomyces olivaceus* ATCC 11009.

* * * * *

UNITED STATES PATENT AND TRADEMARK OFFICE
CERTIFICATE OF CORRECTION

PATENT NO. : 4,201,769
DATED : May 6, 1980
INVENTOR(S) : YASUHIRO ITOH et al

It is certified that error appears in the above-identified patent and that said Letters Patent are hereby corrected as shown below:

Column 1, line 57: "Rectus-Flexibilis" should be italicized.

Column 3, lines 44 and 45: "Streptomyces" and "Rectus-Flexibilis" should be italicized.

Column 4, lines 61-63: delete "Although has been explained the substance No. $17927A_2$ or No. $17927A_1$-producing strain in the foregoing..." and replace with --Although the substance No. $17927A_2$ or No. $17927A_1$-producing strain has been explained in the foregoing...--.

Column 12, line 30: "meidum" should read ---medium---.

Column 18, line 40: after "substance No.", delete "b".

Column 20, lines 39-40: "Streptomyces" should be italicized.

Signed and Sealed this

Seventh Day of October 1980

[SEAL]

Attest:

SIDNEY A. DIAMOND

Attesting Officer  Commissioner of Patents and Trademarks